United States Patent [19]
Rönnberg et al.

[11] Patent Number: 5,814,036
[45] Date of Patent: Sep. 29, 1998

[54] ABSORBENT ARTICLE AND A METHOD FOR ITS MANUFACTURE

[75] Inventors: Peter Rönnberg, Mölndal; Olle Carlbark, Kållered, both of Sweden

[73] Assignee: Mölnlycke AB, Gothenberg, Sweden

[21] Appl. No.: 867,922

[22] Filed: Jun. 3, 1997

Related U.S. Application Data

[63] Continuation of Ser. No. 433,465, filed as PCT/SE93/00963 Nov. 11, 1993 published as WO94/10951 May 26, 1994, abandoned.

[30] Foreign Application Priority Data

Nov. 11, 1992 [SE] Sweden ................................ 9203372

[51] Int. Cl.⁶ .......................... A61F 13/15; A61F 13/20
[52] U.S. Cl. ..................... 604/385.1; 604/385.2
[58] Field of Search ................ 604/385.2, 397, 604/398, 385.1; 156/227, 292

[56] References Cited

U.S. PATENT DOCUMENTS

| | | |
|---|---|---|
| 3,776,233 | 12/1973 | Schaar .................................. 604/385.1 |
| 3,863,637 | 2/1975 | MacDonald et al. ................. 604/385.1 |
| 4,041,950 | 8/1977 | Jones, Sr. .............................. 604/385.1 |
| 4,704,116 | 11/1987 | Enloe .................................... 604/385.2 |
| 4,834,740 | 5/1989 | Suzuki et al. . |
| 4,900,384 | 2/1990 | Sanders et al. ...................... 604/385.2 |
| 5,019,067 | 5/1991 | Simmons . |
| 5,061,261 | 10/1991 | Suzuki et al. . |
| 5,064,421 | 11/1991 | Tracy ....................................... 604/386 |
| 5,080,658 | 1/1992 | Igaue et al. . |
| 5,207,662 | 5/1993 | James ................................... 604/385.1 |
| 5,211,641 | 5/1993 | Roos et al. ........................... 604/385.1 |

FOREIGN PATENT DOCUMENTS

| | | |
|---|---|---|
| 595785 | 4/1990 | Australia . |
| 0145080 | 6/1985 | European Pat. Off. . |
| 7412756-4 | 11/1978 | Sweden . |
| 2214057 | 8/1989 | United Kingdom . |
| 2262873 | 7/1993 | United Kingdom . |
| 2271501 | 4/1994 | United Kingdom . |

*Primary Examiner*—Mickey Yu
*Assistant Examiner*—Bruce E. Snow

[57] ABSTRACT

An absorbent article such as a diaper, an incontinence guard, a sanitary napkin or like article manufactured from a generally rectangular blank is characterized in that leakage barriers are constructed from those folds which are formed in the material as the blank is folded to a desired shape.

20 Claims, 4 Drawing Sheets

ABSORBENT ARTICLE AND A METHOD FOR ITS MANUFACTURE

This application is a continuation of application Ser. No. 08/433,465, filed as PCT/SE93/00963 Nov. 11, 1993 published as WO94/10951 May 26, 1994 now abandoned.

TECHNICAL FIELD

The present invention relates to an absorbent article such as a diaper, an incontinence guard, a sanitary napkin or like article, which is produced from a generally rectangular blank which includes a liquid permeable, inner casing sheet, a liquid impermeable, outer casing sheet, and an absorbent body enclosed between the two casing sheets.

The present invention also relates to a method of manufacturing such an article.

RELATED ART

An article of this kind shall be able to receive body fluid discharged by the wearer without leaking.

Absorbent articles that are intended for one-time use only, for instance children's diapers, adult incontinence guards or sanitary napkins are normally constructed from a layer of non-woven material through which fluids discharged by the wearer are permitted to pass, an absorbent layer of, e.g., fluff pulp, optionally combined with so-called superabsorbents, and a liquid-impervious layer of polyethylene for instance.

Innumerable complicated and often unnecessarily sophisticated diaper constructions have been proposed which have been said to be able to take-up body fluid in a short period of time and to be able to retain large volumes of discharged liquid even under difficult circumstances. The majority of the solutions hitherto proposed do not function with complete satisfaction and also require complicated and intricate manufacturing processes which are hardly compatible with rapid, effective and inexpensive production.

An absorbent article which is intended for one-time use only will preferably be simple to manufacture. Consequently, from the aspect of manufacture, it is desirable that such articles deviate as little as possible from a simple flat and rectangular shape, a shape which, how-ever, is rather poorly adapted to the anatomy of the wearer.

When the wearer suddenly discharges a large quantity of body fluid, the fluid is unable to penetrate the inner casing sheet immediately and be absorbed by the absorbent body. A certain amount of fluid will therefore collect on the surface of the sheet until the time when it is absorbed by the absorbent body.

When the article does not conform effectively to the anatomy of the wearer, there are formed in the absorbent body folds which enable the still unabsorbed fluid to escape from the article, primarily along the lower part of the groin and along the inside of the thighs. Moreover, this problem is often made worse by the wearer's movements.

In order to better adapt absorbent articles to the wearer's crotch, it is normal to give the article an hourglass configuration, i.e. to create a waist in the centre of the rectangular contour. In this case, the narrowest part is dimensioned so as to cover the relatively narrow space at the bottom of the pelvis between the thighs of the wearer when the article is worn, without forming grooves and folds in the material, and the edges of the arcuate, narrowing contour are adapted to conform to the thighs of the wearer in use.

In the case of an hourglass-shaped article, such as a diaper, the majority of the fluid discharged by the wearer shall, in the majority of cases, be taken-up and retained in the narrowest part of the article, which means that the article must have an effective lateral seal against side leakage.

Many attempts have been made to achieve an effective seal, by providing the diaper with elastication which seats tightly against the wearer's thighs. Absorbent articles which have an hourglass configuration and which are provided with leg elastication make manufacture much more difficult and much more expensive, since it is necessary for the tools used to work along curves and crooked paths and since a considerable part of the material is clipped away or folded-in to no useful purpose.

An anatomical configuration of the article in accordance with known methods unavoidably causes some of the material to remain unused, a fact which must be considered incompatible with the high demands placed on the utilization of resources that should be expected in the manufacture of disposable articles.

It would therefore be advantageous if the mutually conflicting desires for anatomical conformity of the article and the optimum use of the material could both be fulfilled at one and the same time.

As will be evident from U.S. Pat. No. 4,883,482, manufacture can be greatly facilitated when the elastication is applied in a manufacturing stage in which the article is still in its original rectangular shape and in which the elastic material can be stretched straight along the side edges of the article. An article constructed in accordance with this publication initially has a rectangular profile and is provided with two parallel elastic threads which extend straight along the side edges and between the inner and the outer sheets. The article is then folded in a manner to obtain a narrowing in the vicinity of its transversal centre axis, wherein the elastic threads are stretched out in an inwardly curved arc on respective edges of the article and along a part of the long sides thereof.

European Patent Specification EP 0,145,080 teaches a similar invention which is intended to improve sealing of the article in the crotch region thereof. This specification also expresses the desire of avoiding mounting an elastic band along a curved line and, instead, suggests that the elastic band is mounted on both sides of the absorbent pad along the long sides thereof in a generally straight, process-friendly configuration, and then to fold the article over its inner surface and join the folds in a punctiform fashion, so that the elastic bands are curved around the leg openings and provide the desired anatomical conformity.

Another known method of attempting to prevent side leakage in the crotch region of the article involves the construction of barriers along the long sides of the absorbent body or the absorbent core as a complement to leg elastication, for instance as described in the European Patent Specification EP 0,219,326. It is assumed that the barriers will be raised on the inside of the article against the wearer's body when the article is in use. When the wearer discharges relatively large volumes of body fluid quickly, not all of the fluid is able to penetrate the inner sheet immediately and be absorbed by the absorbent core. This part of the discharged fluid collects on top of the inner sheet at the enclosed central part of the article and is retained between the erected barriers until it can be absorbed. Such barriers may comprise liquid-impermeable material which is glued or welded along the absorbent body and which is lifted with the aid of the elastic system. The barriers are also particularly suitable for retaining faeces, and barriers which are primarily intended for this purpose need not be impervious to liquid. Although such a construction will enhance the ability of the article to retain excretions, this is achieved at the cost of effective and rapid manufacture.

Further, SE-B-404 868 shows a diaper having a fold line extending along its longitudinal centre axis. Surface portions of the liquid permeable inner casing layer on opposite sides of the longitudinal centre axis are joined together by gluing along symmetrical arcs. This produces a single fold located centrally on the diaper and extending over the outside thereof, i.e. the side distant from the wearer. The formation of the fold results in a decrease in the width of the diaper, thus forming a narrower crotch portion. The additional material gathered in the fold will increase the absorption capacity in that region. The fold is also said to form a pocket for collecting faeces and preventing spreading thereof. However, more material is gathered in the fold than is warranted for the purpose of increasing the absorption capacity, and this results in a bulky mid-section and thus an uncomfortable diaper.

SUMMARY AND OBJECTS

Thus, many complicated solutions have resulted in far too complicated and progressively more expensive disposable products. The object of the present invention is to provide an equally effective seal with the aid of less costly and simpler means.

In an inventive absorbent article, the blank is folded along at least two fold lines located on the outer casing sheet between one of said centre lines and a respective one of the associated opposing side edges; whereby two folds are formed on the inside of the article, each extending along a side edge thereof so that the folds when raised on the inside of the article form leakage-prevention barriers whose height is essentially proportional to the decrease of the dimension of the article transverse the associated fold line obtained by the formation of the fold.

The present invention is based on the concept of creating leakage barriers from those folds which occur in the material when the original rectangular blank, from which the article is produced, is folded into a desired shape.

That material which is no longer used laterally is used vertically instead.

In one preferred embodiment, the original rectangular shape of the blank is formed to an hourglass shape, wherein the gathered material forms a fold on each side of the longitudinally extending centre axis of the article.

These folds are at their highest where the arcuate narrowing has its maximum value, which in the case of a diaper is in the vicinity of the transverse centre axis of the article. The mutually facing parts of the fold are joined together on the outside of the article and are raised on the inside of said article, therewith creating leakage barriers while obtaining an anatomical conformity at the same time. In this way, an effective lateral seal can be combined with total use of the material and a radical simplification in manufacture.

The height of the barriers is defined as the distance between the fold baseline and the fold folding line as measured perpendicularly to said fold line, and varies along the length of the barriers while being generally proportional to the dimensional change that occurs transversely to the fold when folding the material.

In a preferred embodiment, the barriers preferably extend along two fold lines which extend symmetrically on both sides of the longitudinally extending centre axis of the article over at least a part of the length of the article, although while crossing the transverse centre axis thereof. Although the fold lines are preferably straight, they may also be arcuate, either inwardly or outwardly, continuously curved, or may consist of several mutually adjacent rectilinear segments. The fold lines may be parallel with the longitudinal centre axis of the article or may converge so that the fluid-receiving surface delimited therebetween will vary along the length of the article. The fold lines are preferably located on side flaps outside the edges of the absorbent body. These side flaps include both of the aforesaid casing sheets or solely one of said sheets. The side flaps may also consist of a casing material which is different to the remainder of the casing material, preferably a breathable, vapour-permeable material, or some other skin-friendly material which can be easily joined to the rectangular blank before bringing the blank to its final shape.

An advantage is gained when at least the inner join line extends out over the absorbent body. The barriers will then include a part of the absorbent body material. Manufacture is greatly facilitated when roll material is used to produce the absorbent body, since the three different material layers of the article can then be advanced from three different, continuous material webs. Two join lines extend symmetrically on both sides of each fold line, or when the fold line is curved, are located at the same distance from said fold line in a direction perpendicular thereto, and are brought together to form the baseline of the fold and are joined to one another in conjunction with making the fold, so as to give the article its definitive, three-dimensional shape. The join lines may also be located asymmetrically on respective sides of the fold line. For instance, one of the fold lines may be curved and the other straight, or both join lines may be curved but with different radiuses of curvature. This will mean that the material in the resultant fold will be stretched to a greater extent in one side of the fold, or that one side of the fold will be stretched and the other pleated. This will create in the material tension forces which force the fold to rise to an intended position.

In one suitable embodiment, the fold lines are straight and the join lines are arcuate. As mentioned above, the heights of the barriers vary in the longitudinal direction in mutually the same manner along both of the fold lines, and will conveniently be at their highest in the vicinity of the transverse centre axis of the article, with a continuously decreasing value towards the two end edges of the article. The join lines may also be composed of several, closely adjacent straight segments. The join lines may cross associated fold lines, i.e. the fold may be partially raised on the rear side of the article. Constructions which include several join lines on both sides of a fold line, or a series of alternating fold and join lines or the like, i.e. barriers which are comprised of several folds or pleats, are of course conceivable, as are also constructions in which, subsequent to forming the fold, the fold line is combined with the fold baseline to form a lower, thicker fold, or alternatively a hose-like fold.

The two inwardly lying join lines, i.e. the join lines that are located in the central receiving zone of the article extend conveniently out over the absorbent body, at least partially, so that the resultant barrier will include a part of the absorbent body material, from its base and up to a given level along its height and also along the whole of its length.

Consequently, the smallest distance between the two inner join lines is obtained where the barrier has its maximum height, said distance being dimensioned to cover the crotch region of the contemplated user. The barrier height as a function of the position in the longitudinal direction will thereafter determine the final shape of the article. In the proposed example, the barrier height decreases symmetrically and continuously in a convex curve, from its maximum value at the transverse centre axis of the article to a zero value at the point where the fold line and the join lines are combined. This corresponds to an arcuate narrowing of the shape or profile of the article. A conceivable alternative is a curve shape which decreases symmetrically first in a convex arc, then in a slightly concave arc and finally flattens into a straight line at the end edges of the article. Other variations are, of course, permitted. In general, the final width b of the article as a function of the position in the longitudinal direction x can be expressed as: $b(x)=B-4h(x)$, where B is the original width of the article and $h(x)$ is the barrier height as a function of the position in the longitudinal direction.

It is also desirable that the maximum value of the barrier height will not exceed the value of the smallest distance between the outer join line and the side edge of the article, in order to prevent the leakage barrier from extending beyond the side edge of the article when the article is in use, should the barrier be unintentionally folded down against said edge.

A pretensioned elastic element, such as an elastic thread, band or the like, can be mounted along the fold lines or between two join lines which are associated with one and the same fold line, such that the elastic element will extend along and within the barrier after joining the fold. These elements can be fastened to the article in a punctiform fashion, with the points so selected that the elements tend to contract when the article is curved in connection with putting it on, therewith assisting in holding the barriers in a raised position. These elastic elements can be mounted between the casing sheets, e.g. on the inner casing sheet, on the side thereof which lies proximal to the outer casing sheet, where a small fold or sleeve may be arranged for accommodating the elastic elements. Alternatively, the elastic elements may be mounted on the outside of the article, i.e. on the outer surface of the outer casing sheet.

The article may also be provided with one or more pretensioned elastic elements, such as elastic threads, bands or the like, along at least a part of the long sides of the rectangular blank. In conjunction with forming the fold and the resultant change in shape, these elastic elements are curved along the arcuate, narrowing sides so that when the article is worn, they will endeavour to contract around the wearer's thighs and function as tightly seating leg elastic. An element, such as a band, strip or the like, preferably made of an elastic material, such as foam plastic, elastic non-woven fabric or the like, can also be mounted along the long sides of the blank and folded over along the edges thereof. In this way, there is formed a hose-like fold having loop-like cross-section which extends along the edge of the article. Further elastic elements can be mounted within this fold and function as leg elastic when the article is worn.

When the article is a diaper or an incontinence guard, the article is fastened with the aid of adhesive tape, burr-type fastener bands or the like, either at the front and rear part of the article around the waist of the wearer, or to a reusable belt. When the article is fastened to a reusable belt, the belt is covered with, for instance, looped burr fastener devices, whereas the article is provided with hooked burr-fastener bands at the corners or along the waist parts of the article.

BRIEF DESCRIPTION OF THE DRAWINGS

The invention will now be described in more detail with reference to exemplifying embodiments thereof and also with reference to the accompanying drawings, in which.

DETAILED DESCRIPTION OF THE PREFERRED EMBODIMENTS

Figure 1:
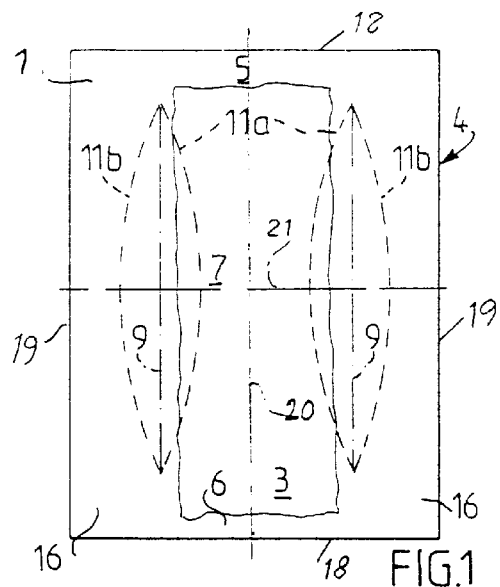
FIG. 1 illustrates a first and preferred embodiment of the invention.

The figures illustrate diapers or incontinence guards which include an inner casing sheet 1 of liquid-permeable material, suitably non-woven material, an outer casing sheet 2 of liquid-impermeable material, for instance polyethylene film, and an absorbent body or pad 3 which is enclosed between the casing sheets. The absorbent body 3 may be comprised of cellulose fluff pulp which includes superabsorbent material in fibre or particle form.

The blank 4, which includes the casing sheets and the absorbent body, is originally rectangular in shape and has transverse side edges 18, longitudinal side edges 19, a longitudinal centre axis 20 and a transverse centre axis 21. Parts of the casing sheets protrude beyond the absorbent body and said sheets are mutually joined at said protruding parts. The blank 4 has a front part 5, a rear part 6 and a crotch part 7. A fold 8 is formed by folding the blank along fold lines 9 and by bringing together join lines 11a and 11b, see FIGS. 1–5, on both sides of the fold line and joining said fold lines in a baseline 12, see FIGS. 6–9. The join lines 11 may be joined together in a punctiform fashion or may be joined continuously along the whole of the base line. It is also conceivable to bond together over the whole of their surfaces those parts of the outer casing sheet which lie in mutual abutment in the folds.

Figure 6:
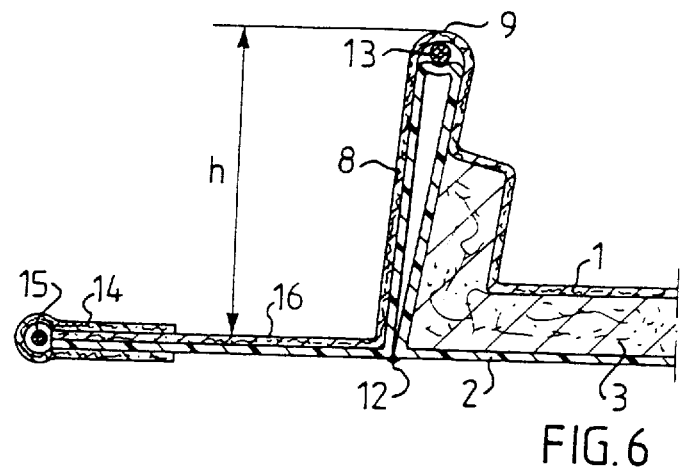
FIG. 6 is a broken cross-sectional view of the blank 4 of FIG. 1 and shows the blank in a finished state.
Figure 7:
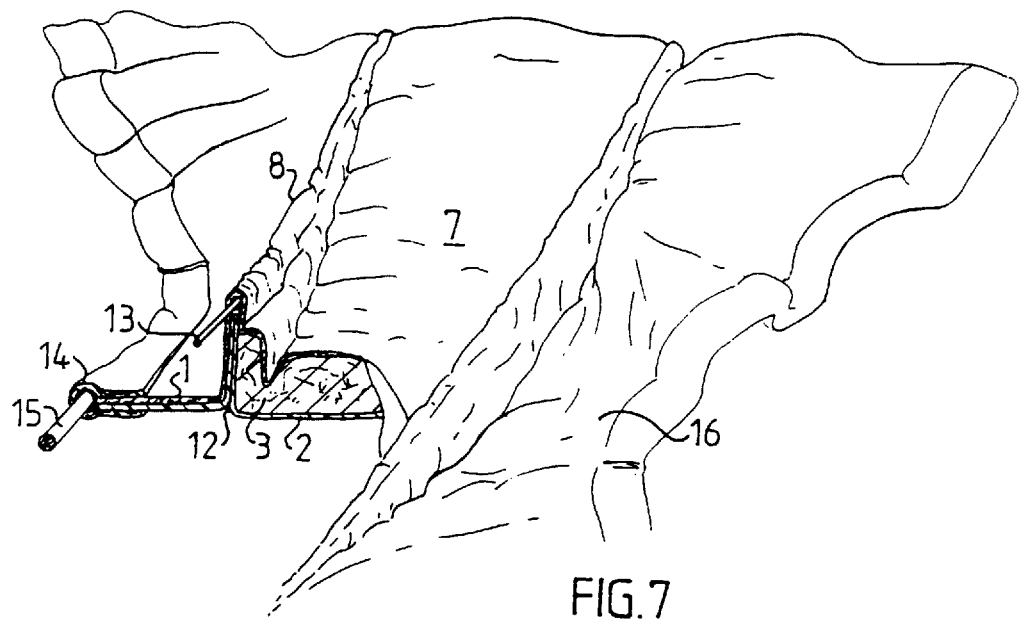
FIG. 7 is a perspective view of the proposed exemplifying embodiment of FIG. 1.
Figure 8:
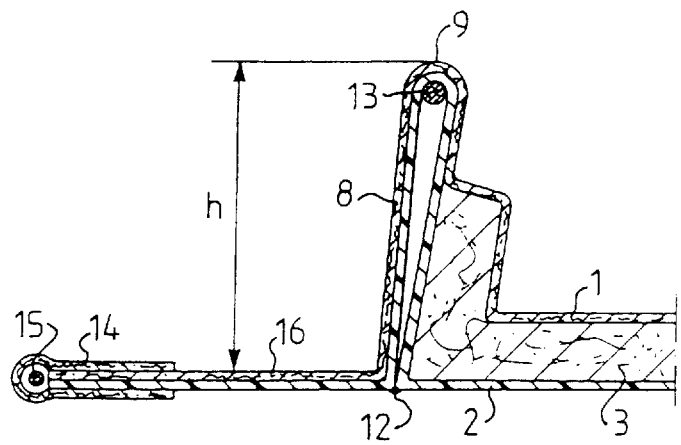
FIGS. 8 and 9 are views like that in FIG. 6 of alternative embodiments to that shown in FIGS. 6 and 7.
Figure 9:
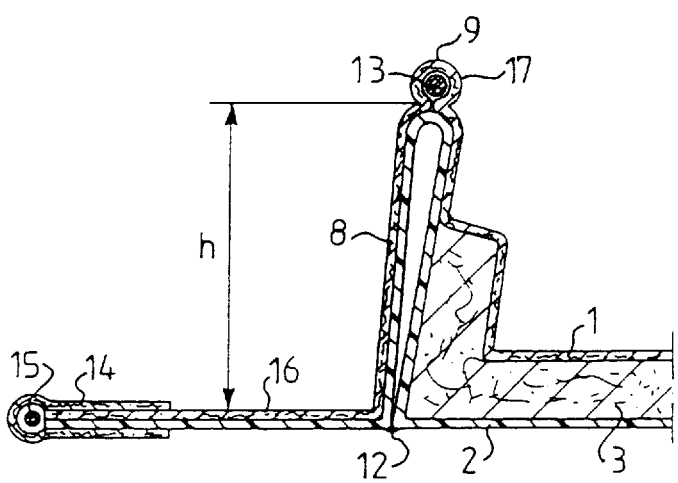

A pretensioned elastic thread 13 is mounted in the fold 8, either between the casing sheets 1 and 2 as shown in FIGS. 6 and 7, on the outside of the outer casing sheet 2 as shown in FIG. 8, or within a further fold 17 in the inner casing sheet 1, as shown in FIG. 9. The elastic thread 13 assists in holding the fold raised, essentially at right angles to the plane of the blank 4. A pretensioned elastic band 14, conveniently an elastic foam material, is mounted along the side edges 19 of the blank 4, this band being folded around the edge parts of the casing and forming a hose-like fold having a loop-like cross-section, as shown in FIGS. 6–9. A pretensioned elastic thread 15 is mounted in said fold.

The folds 8 form barriers which prevent urine and faeces from spreading further laterally. When the article is worn, the edge parts of the casing sheets formed outside the folds are intended to embrace the wearer's legs, at least the insides of the wearer's thighs, said elastic devices 14, 15 functioning as leg elastic and sealing against undesirable leakage around the wearer's leg.

Figure 10:
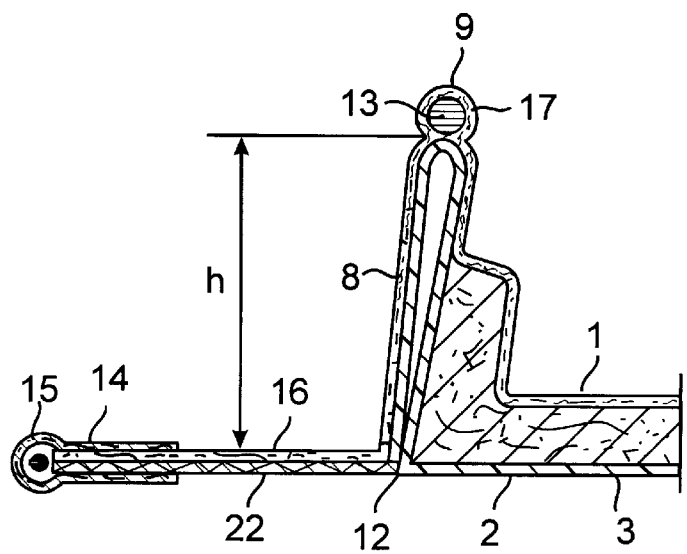
FIGS. 10 and 11 are views like that of FIG. 6 illustrating alternative embodiments of the present invention.
Figure 11:
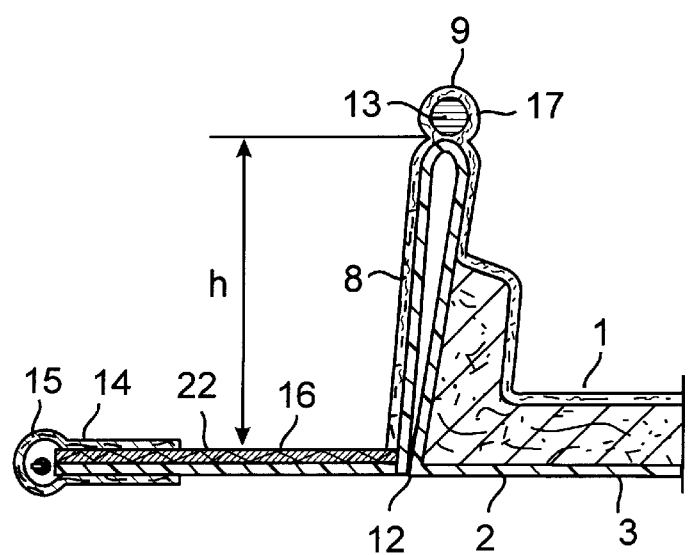

FIG. 1 illustrates a configuration in which each of two parallel fold lines 9 extends on a respective side of the absorbent body 3. The join lines 11a and 11b are arcuate in shape and the distance between said lines and the associated fold line is greatest where the width of the article is intended to be smallest, i.e. in the vicinity of the transverse centre axis 21. However, the distance between the outer join line 11b and the edge 19 of the article is greater at this point than the distance between the join line 11b and the fold line 9, so as to prevent the barrier from extending beyond the side edge of the article when the article is worn, should the barrier be unintentionally folded down onto said side edge. The inner join lines 11a extend partially in over the absorbent body 3, and the barriers will therefore include a part of the absorbent body, as illustrated in the cross-sectional views of FIGS. 6–9. The outer join lines 11b extend along side flaps 16 outside the edges of the absorbent body 3. These side flaps 16 include both casing sheets 1, 2. As shown in FIGS. 10 and 11, the side flaps 16 may also consist of casing material 22 than the remainder of the casing, preferably a breathable, vapour-permeable material or some other kind of skin-friendly material which can be readily joined to the rectangular blank 4 prior to shaping the blank to its final hourglass shape. Such vapour-permeable material may, for instance, consist solely of the inner casing sheet. The absorbent body may also extend over the entire surface of the blank.

Figure 2:
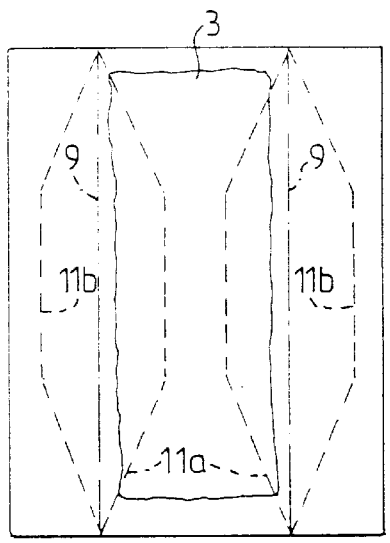
FIGS. 2–5 illustrate modified embodiments.

FIG. 2 illustrates a variation of the configuration shown in FIG. 1, in which the fold lines 9 extend along the full length of the article and in which the join lines 11 are comprised of three mutually sequential straight join-line parts.

Figure 3:
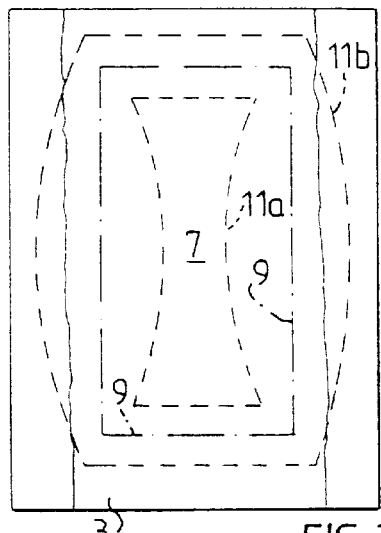

FIG. 3 illustrates a configuration comprising four fold lines 9, of which two lines extend in the transverse direction of the article and two lines extend in the longitudinal direction of the article. The fold lines 9 enclose a central receiving zone 7 and extend in over the absorbent body 3.

Figure 4:
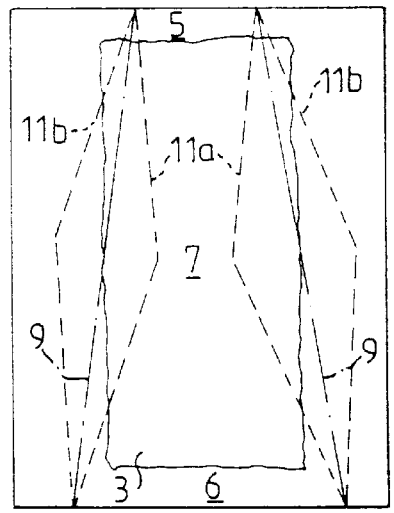

FIG. 4 illustrates a variant in which two non-parallel fold lines 9 extend symmetrically on a respective side of the absorbent body 3 and lie partially on said body. The size of the central receiving surface 7 varies along the length of the article and a larger surface is delimited, for instance, on the rear part 6 of the article for collecting faeces in the case of adult incontinence guards. The join lines 11a and 11b are comprised of two straight segments.

Figure 5:
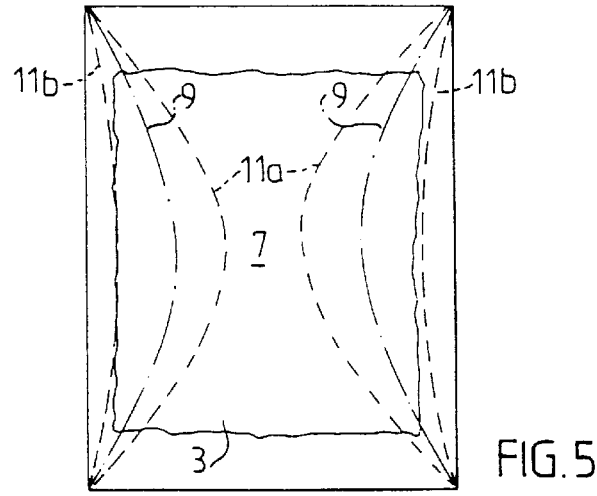

FIG. 5 illustrates an alternative which includes two curved fold lines 9 and join lines 11a and 11b which are located asymmetrically adjacent thereto. This configuration is also suitable for sanitary napkins, panty protectors and like articles.

FIG. 6 is a cross-sectional view of one of the barriers included in the article and shows the blank in a folded state in accordance with FIG. 1, for example. The fold line 9 forms the top of the barrier and the baseline 12 is the line along which the two join lines 11a and 11b are joined. The join lines are joined together with the aid of an adhesive, by welding or some like technique, and are joined in a punctiform fashion or continuously along the whole of the baseline 12, optionally on a part of the mutually facing surfaces of the outer casing sheet 2 or over the whole of these surfaces. The elastic element 13 is mounted along and within the fold 8, between the inner casing sheet 1 and the outer casing sheet 2, and is fastened to the article at points which are so chosen as to assist in holding the fold 8 in a raised state. This element 13 may alternatively be arranged on the outer surface of the outer sheet 2, as shown in FIG. 8, or within a further fold 17 formed in the inner sheet 1, as shown in FIG. 9. The absorbent body 3 extends into the fold 8, so as to strengthen the fold and to enhance its leakage-prevention ability. The elastic element 15, which is intended to function as leg elastic, extends within a hose-like fold 14 having a loop-like cross-sectional shape. This fold 14 is formed from a broad band of skin-friendly material of a type different to the remaining casing material. The material band 14 may cover the whole of the side flaps 16 or a part thereof and may also be fastened to the edge of the casing material in the vicinity of the baseline 12 and extend beyond this edge to form further side flaps. A broad material band 14 can be applied to the side edges of the rectangular blank 4 much more readily than when the same band is applied along curved surfaces.

It will be understood that the invention is not restricted to the aforedescribed exemplifying embodiments thereof and that other modifications are conceivable within the scope of the following claims. Although the invention has been described above with reference to examples of diaper or incontinence guard configurations, it will be understood that the invention can also be applied to produce a sanitary napkin from a rectangular blank in the same manner, narrowing proportionally with the barrier height. As illustrated in FIG. 3, the article need not only include longitudinally extending barriers, but also barriers which extend in other directions.

An article constructed in accordance with the invention can be produced very simply. The absorbent body may conveniently be comprised of roll material, for instance a continuous web of cellulose fibre, optionally admixed with reinforcing thermoplastic fibres. The roll material may also be comprised of a number of tissue layers which enclose superabsorbent particles. The roll material may also be a foam material, optionally with an admixture of superabsorbent material.

We claim:

1. An absorbent article comprising:

a generally rectangular blank including a liquid permeable inner casing sheet, a liquid impermeable outer casing sheet, said sheets each having a first surface and a second surface, said first surface of the inner casing sheet facing said first surface of the outer casing sheet, and an absorbent body enclosed between the first surfaces of the two casing sheets, the blank having two mutually opposing transverse side edges, two mutually opposing longitudinal side edges extending between the transverse side edges, and a longitudinal center axis extending intermediate the longitudinal side edges;

at least two fold lines, each of which fold lines are located between the longitudinal center axis and a respective one of the associated opposing longitudinal side edges;

an inner join line and an outer join line which prior to folding extend on opposite sides of each of the fold lines on the outer casing sheet, wherein the inner and outer join lines on the outer casing sheet associated with each fold line are brought together and joined to form at least two folds raised above the second surface of said inner casing sheet;

a dimension of the article taken in a direction transverse to the fold lines varying along a length of the article due to the relative locations of the fold lines and the join lines, whereby at least two folds are formed on the inside of the article and form leakage-prevention barriers whose height is essentially inversely proportional to the dimension of the article in the direction transverse to the associated fold line obtained by the formation of the fold;

wherein the inner join line associated with one of the fold lines extends at least partially over the absorbent body, such that the absorbent body extends into the leakage-prevention barrier formed by the fold;

said article in a folded state including a front part, a back part and a narrower part which is narrower than at least one of said front and back parts, and the join lines having an arcuate shape such that the height of the leakage prevention barriers decreases at least in one direction toward either the front part or back part from a maximum height in the narrower part of said article;

a distance between the outer join line located nearest the longitudinal side edge of the article and the associated fold line at each point along said fold line is smaller than the distance between this join line and the longitudinal side edge, such that flexible side flaps are formed between each of the leakage-prevention barriers and the longitudinal side edges; and at least one elastic element provided at each longitudinal side edge of the blank, said elastic element forming a curved leg elastic tending to contract around a wearer's legs when the article is worn.

2. The article according to claim 1, wherein the two fold lines extend as straight lines on opposite sides of the longitudinal centre axis of the article.

3. The article according to claim 2, wherein the fold lines extend parallel with the longitudinal centre axis of the article.

4. The article according to claim 1, wherein the arcuate shape of the join lines is formed by several mutually adjacent straight segments.

5. The article according to claim 1, wherein each fold is provided with at least one elastic element which is mounted in a tensioned state within and along the fold and assists in holding the barrier formed by the fold in a raised state when the article is worn.

6. The article according to claim 5, wherein the elastic element is mounted on the outside of the outer casing sheet.

7. The article according to claim 5, wherein the elastic element is mounted between the inner and the outer casing sheets.

8. The article according to claim 5, wherein the elastic element is mounted on the inner casing sheet on its side facing towards the outer sheet in a further fold formed in the inner sheet.

9. The article according to claim 5, wherein the at least one elastic element is selected from the group consisting of an elastic thread and an elastic band.

10. The article according to claim 1, wherein one of the inner casing sheet and the outer casing sheer extends further from the absorbent body than the other of the inner casing sheet and the outer casing sheet.

11. The article according to claim 1, wherein the rectangular blank has side flaps of casing material which are comprised of a material different than a remainder of the casing.

12. The article according to claim 11, wherein the side flaps are comprised of a vapor-permeable material.

13. The article according to claim 1, wherein a band-shaped element made of at least one of foamed plastic and non-woven fabric is mounted on one side surface of each longitudinal edge of the blank, such that part of the width of the band-shaped element will extend beyond the edge of the blank, where it is folded over and fastened to the opposite side surface of said edge.

14. The article according to claim 1, wherein the absorbent body is comprised of roll material.

15. The absorbent article of claim 1 wherein the inner join line and the outer join line extend on the second surface of the outer casing sheet such that the inner and outer join lines on the second surface of the outer casing sheet associated with each fold line are brought together and joined to form the at least two folds.

16. An absorbent article comprising:

a generally rectangular blank including a liquid permeable inner casing sheet having an inner surface and an outer surface, a liquid impermeable outer casing sheet having an inner surface and an outer surface, and an absorbent body enclosed between the inner surfaces of said two casing sheets, the blank having two mutually opposing transverse side edges, two mutually opposing longitudinal side edges extending between the transverse side edges, and a longitudinal center axis extending intermediate the longitudinal side edges;

at least two fold lines, each of which fold lines are located between the longitudinal center axis and a respective one of the associated opposing longitudinal side edges;

an inner join line and an outer join line which prior to folding extend on opposite sides of each of the fold lines on the outer casing sheet, wherein the inner and outer join lines on the outer casing sheet associated with each fold line are brought together and joined to form at least two folds raised above the outer surface of said inner casing sheet, with at least one said fold being located on each side of the longitudinal center axis;

a dimension of the article taken in a direction transverse to the fold lines varying along the length of the article due to the relative locations of the fold lines and the join lines, whereby at least two folds are formed on the inside of the article and form leakage-prevention barriers whose height is essentially inversely proportional to the dimension of the article in the direction transverse to the associated fold line obtained by the formation of the fold;

wherein the inner join line associated with one of the fold lines extends at least partially over the absorbent body, such that the absorbent body extends into the leakage-prevention barrier formed by the fold;

said article in a folded state including a front part, a back part and a narrower part which is narrower than at least one of said front and back parts; and a distance between the outer join line located nearest the longitudinal side edge of the article and the associated fold line at each point along said fold line is smaller than the distance between this join line and the longitudinal side edge, such that flexible side flaps are formed between each of the leakage-prevention barriers and the longitudinal side edges.

17. The absorbent article of claim 16 wherein the inner join line and the outer join line extend on the outer surface of the outer casing sheet such that the inner and outer join lines on the outer surface of the outer casing sheet associated with each fold line are brought together and joined to form the at least two folds.

18. A method of manufacturing absorbent articles, which are formed from a generally rectangular blank which includes a liquid permeable inner casing sheet and a liquid impermeable outer casing sheet, each of said sheets having an inner surface and an outer surface, said inner surfaces facing one another, and an absorbent body which is enclosed between the inner surfaces of said two casing sheets, the blank having two mutually opposing transverse side edges, two mutually opposing longitudinal side edges extending between the transverse side edges, a longitudinal center axis extending intermediate the longitudinal side edges comprising the steps of:

advancing the blanks in a continuous web with at least the casing sheets of individual blanks being mutually continuous;

providing at least one elastic element at each of said longitudinal side edges of the blank;

providing two fold lines, each of which fold lines are located between the longitudinal center axis and a respective one of the associated opposing side edges;

folding the blank along the two fold lines by bringing together and joining about each of the two fold lines the outer casing sheet along two join lines, which prior to folding extend on respective sides of the respective fold line on the outer casing sheet such as to form a respective baseline along which the folded blank is joined together, to form a respective fold extending above the outer surface of said inner casing sheet;

choosing the join lines in relation to the fold lines so as to obtain a desired variation in a dimension of the article transversely to the fold line along the length thereof by formation of the fold;

whereby two folds are formed on an inside of the article, each extending along a side edge thereof so that the folds when raised on the inside of the article form leakage-prevention barriers whose height is essentially proportional to a decrease of the dimension of the article transverse to the associated fold line obtained by the formation of the respective fold;

wherein at least an inner one of the two join lines associated with the fold line extends at least partially over the absorbent body, whereby the absorbent body extends into the barrier formed by the fold; and wherein the join lines are arcuate in shape such that a distance between the join line located nearest the longitudinal side edge of the article and the fold line at each point along said fold line is smaller than the distance between this join line and the longitudinal side edge.

19. The method of claim 18 wherein folding the blank includes bringing together and joining the outer surface of the outer casing sheet along the two join lines to thereby form the respective fold.

20. The method of claim 18 wherein the inner casing sheet extends in a plane and the respective fold extends generally perpendicular to the plane of the inner casing sheet.

* * * * *